United States Patent
Okazaki et al.

(10) Patent No.: US 6,268,333 B1
(45) Date of Patent: Jul. 31, 2001

(54) SEDATIVE EFFECT-PROVIDING FRAGRANCE MODIFIER

(75) Inventors: Yoshiro Okazaki; Yasuhiro Takashima; Shoji Nakamura; Katsuyuki Yomogida; Masahiro Tanida, all of Kanagawa (JP)

(73) Assignees: Takasago International Corporation; Shiseido Company, Limited, both of Tokyo (JP)

( * ) Notice: Subject to any disclaimer, the term of this patent is extended or adjusted under 35 U.S.C. 154(b) by 0 days.

(21) Appl. No.: 08/390,412

(22) Filed: Feb. 17, 1995

Related U.S. Application Data

(63) Continuation of application No. 08/126,195, filed on Sep. 24, 1993, now abandoned.

(30) Foreign Application Priority Data

Sep. 25, 1992 (JP) .................................................. 4-279291

(51) Int. Cl.[7] ............................................................. A61K 7/46
(52) U.S. Cl. ................................. 512/20; 424/401; 512/1; 512/5; 512/8
(58) Field of Search ................................ 424/401; 512/1, 512/5, 8, 20

(56) References Cited

U.S. PATENT DOCUMENTS

| | | | |
|---|---|---|---|
| 4,313,856 | * 2/1982 | Kaiser et al. | 252/522 |
| 4,426,332 | 1/1984 | Thoemel et al. | 260/465 F |
| 4,670,264 | * 6/1987 | Warren et al. | 424/195.1 |
| 4,670,463 | * 6/1987 | Warren et al. | 514/464 |
| 4,671,959 | * 6/1987 | Warren et al. | 424/195.1 |
| 4,952,559 | * 8/1990 | Login et al. | 512/10 |
| 5,023,020 | * 6/1991 | Machida et al. | 261/18.1 |
| 5,141,921 | * 8/1992 | Sawane et al. | 512/26 |

FOREIGN PATENT DOCUMENTS

| | | |
|---|---|---|
| 61-43106 | * 3/1986 | (JP) . |
| 295954 | * 11/1997 | (JP) . |
| 86478 | * 3/2000 | (JP) . |

OTHER PUBLICATIONS

*Perfumer & Flavorist*, vol. 12, Jun./Jul. 1987, pp. 43–45.
*Journal of Chromatography*, 466 (1989), 301–306.
*J. Ess Oil Res.*, 2, 85–90, (Mar./Apr., 1989).
Script of The 10th Takasago Symposium, "The Physiological and Psychological Effects of Odors on Humans" pp. 1–15, which was held May 13, 1992 (issued on Jan. 31, 1993).

* cited by examiner

Primary Examiner—Robert H. Harrison
(74) Attorney, Agent, or Firm—Sughrue, Mion, Zinn, Macpeak & Seas, PLLC

(57) ABSTRACT

A fragrance composition which contains 1,3-dimethoxy-5-methylbenzene in an amount of from 0.01 to 30% by weight as a fragrance modifier that provides a sedative effect. 1,3-Dimethoxy-5-methylbenzene used in the present invention can exhibit a sedative effect not only by itself but also when mixed with various formulations of jasmine, floral and the like types having stimulative effects. Also, since a single chemical is used as an active ingredient, the present invention is more effective than the sedative function of natural essential oil from a viewpoint of sedation. In addition, since 1,3-dimethoxy-5-methylbenzene itself has a mild scent, its sedative effect can be obtained without altering original fragrance of interest.

8 Claims, 7 Drawing Sheets

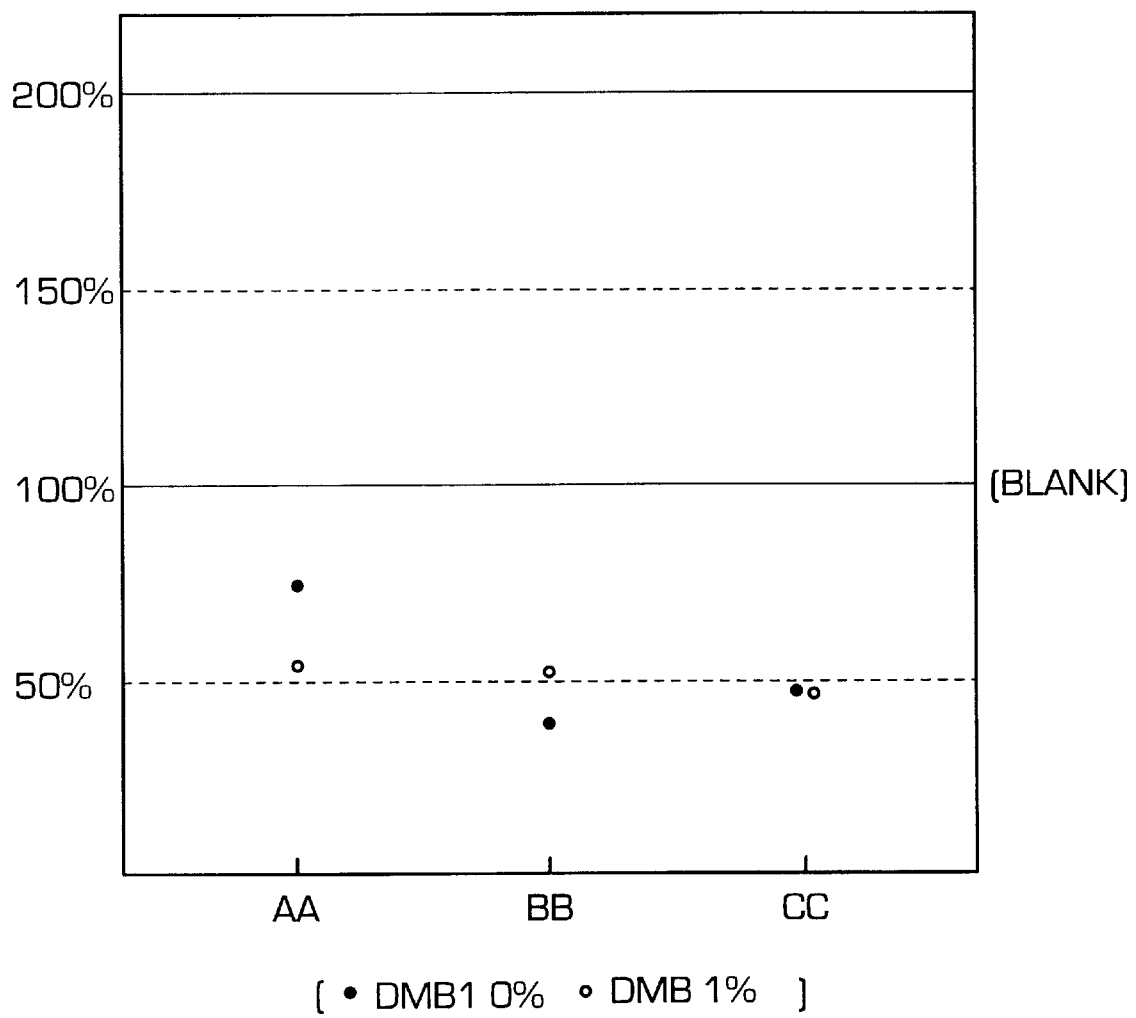

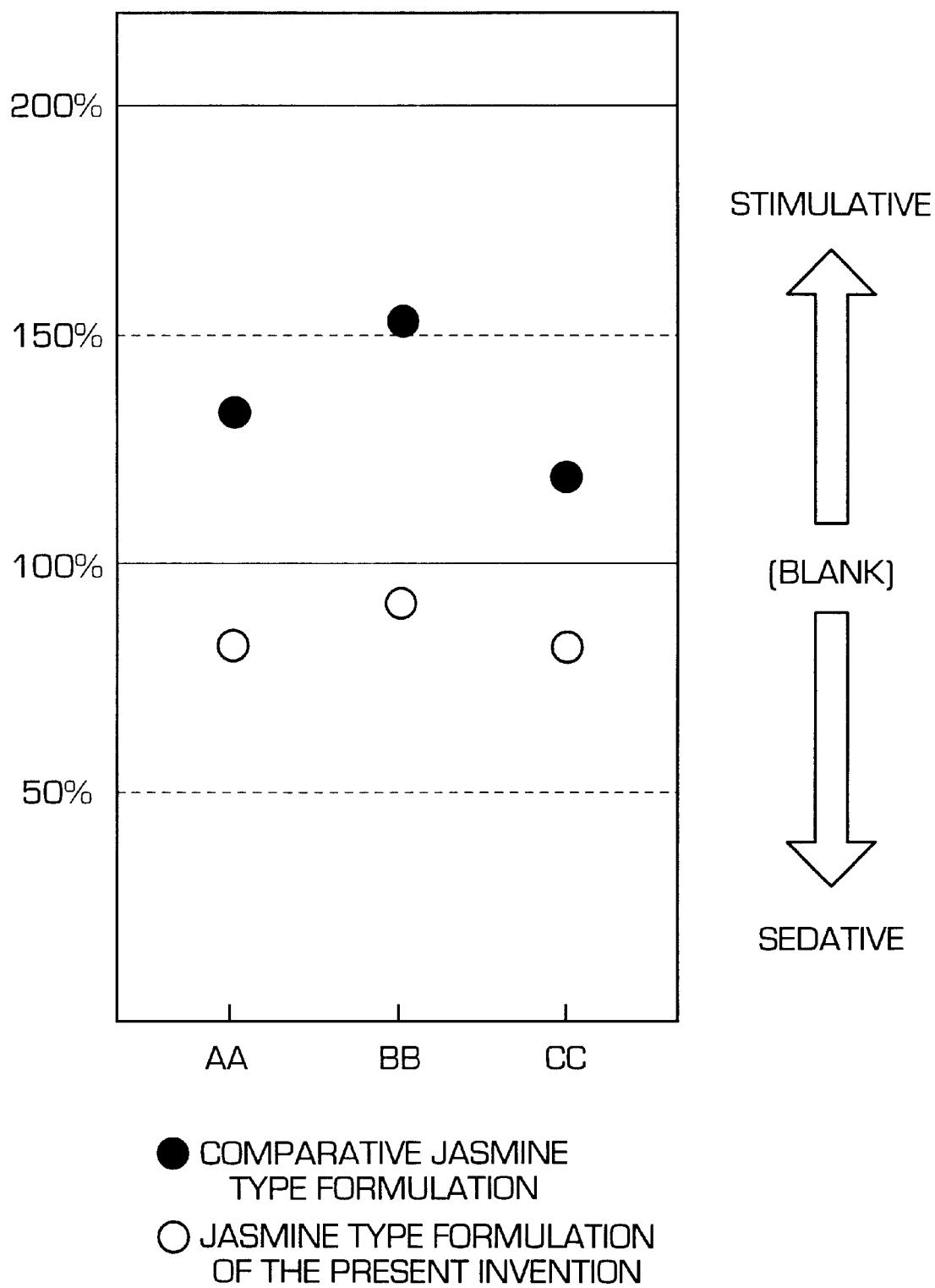

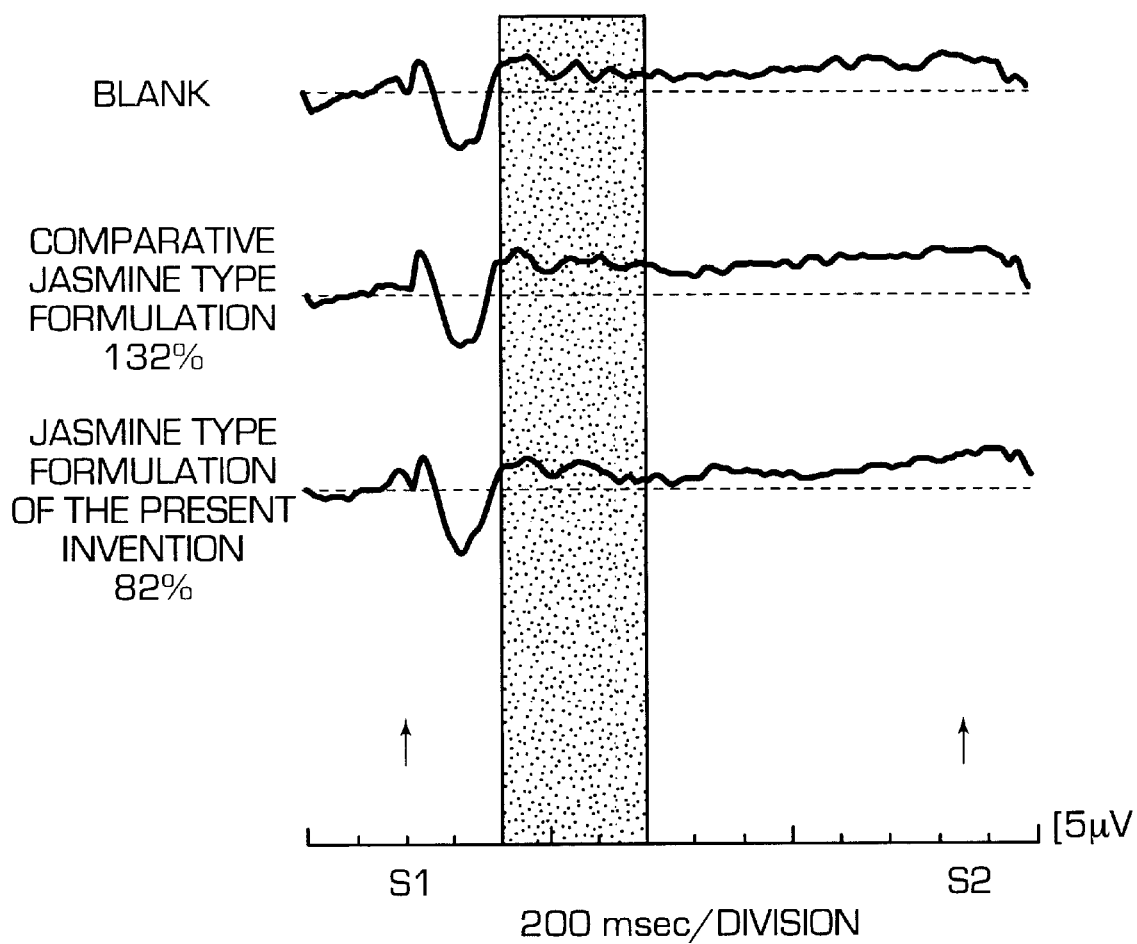

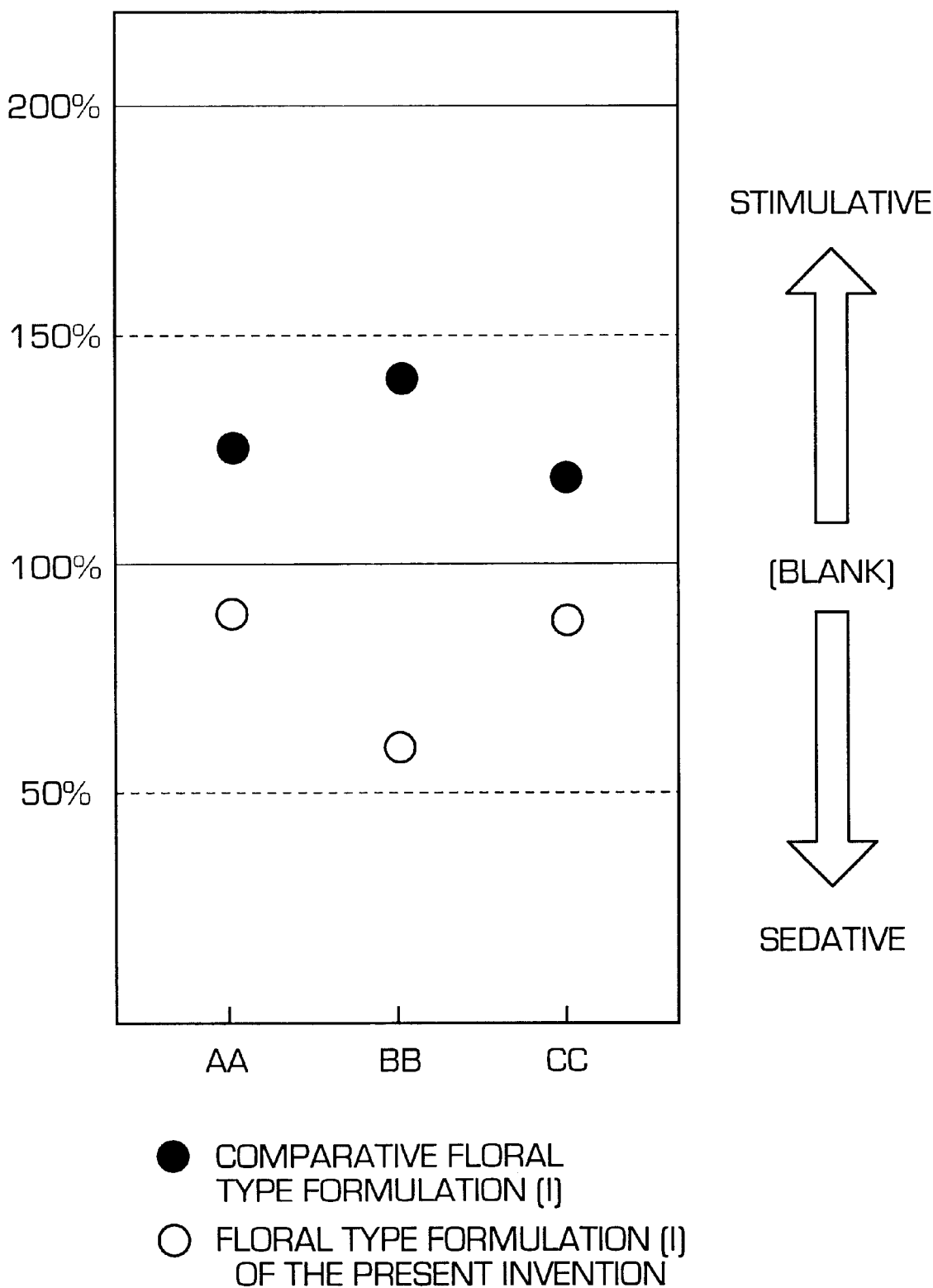

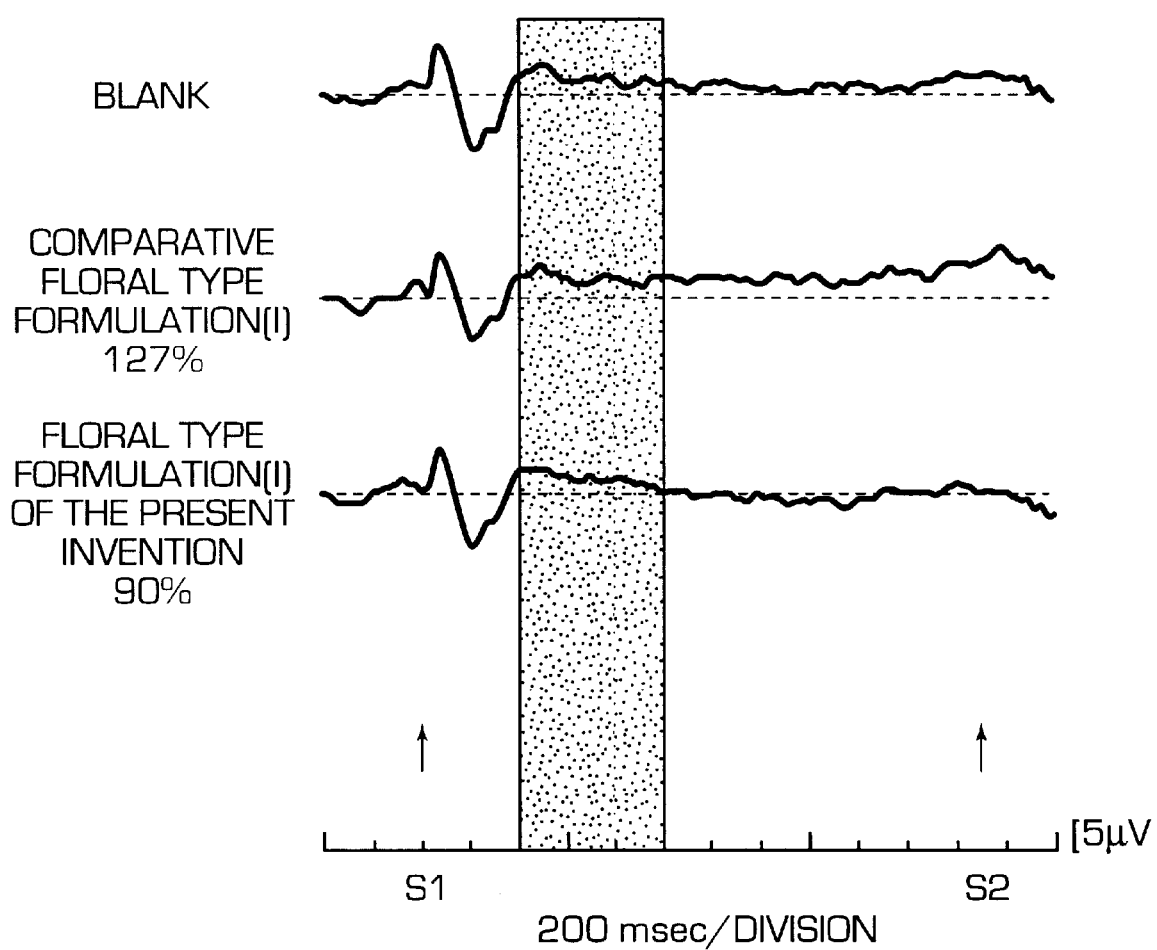

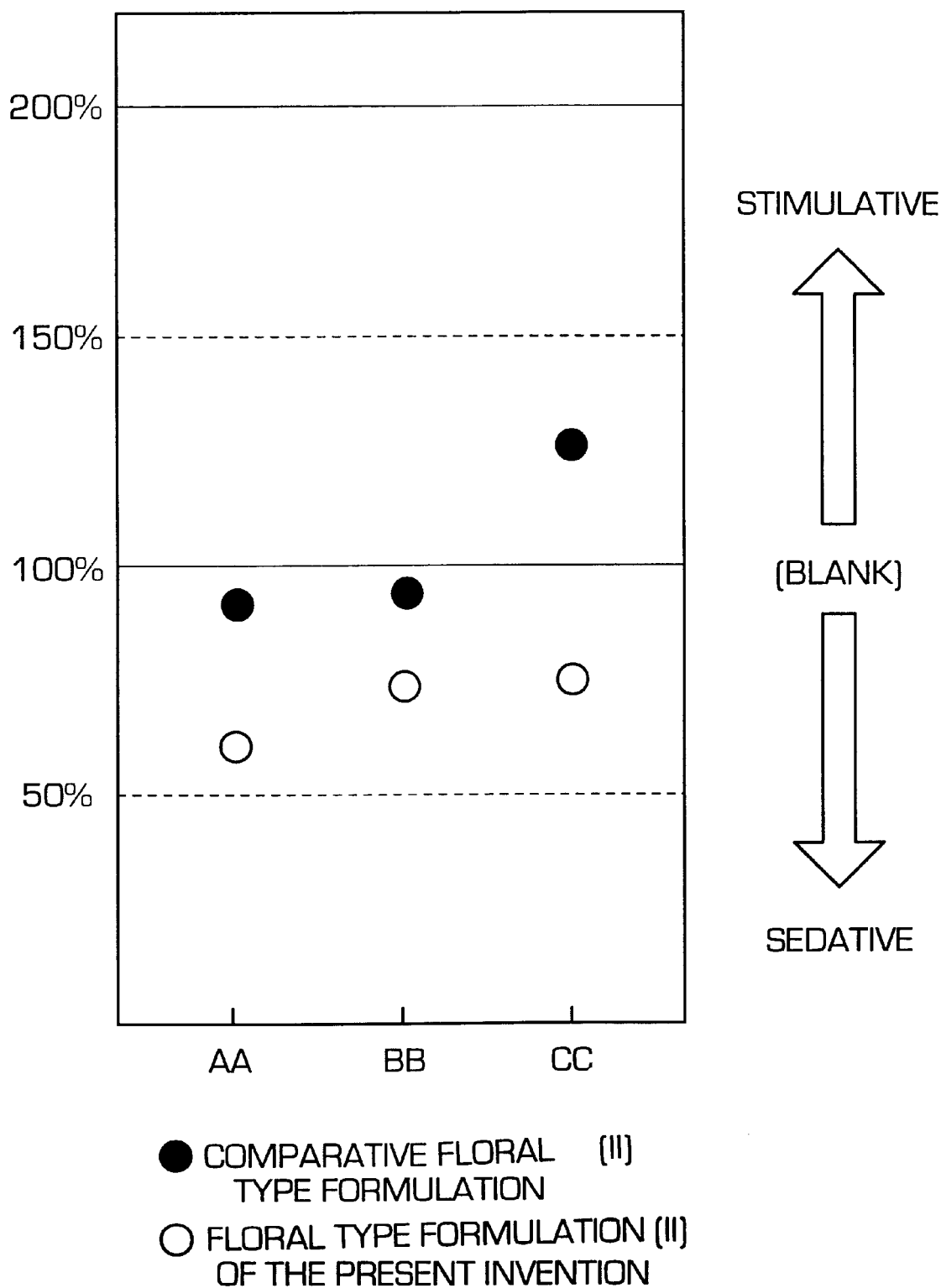

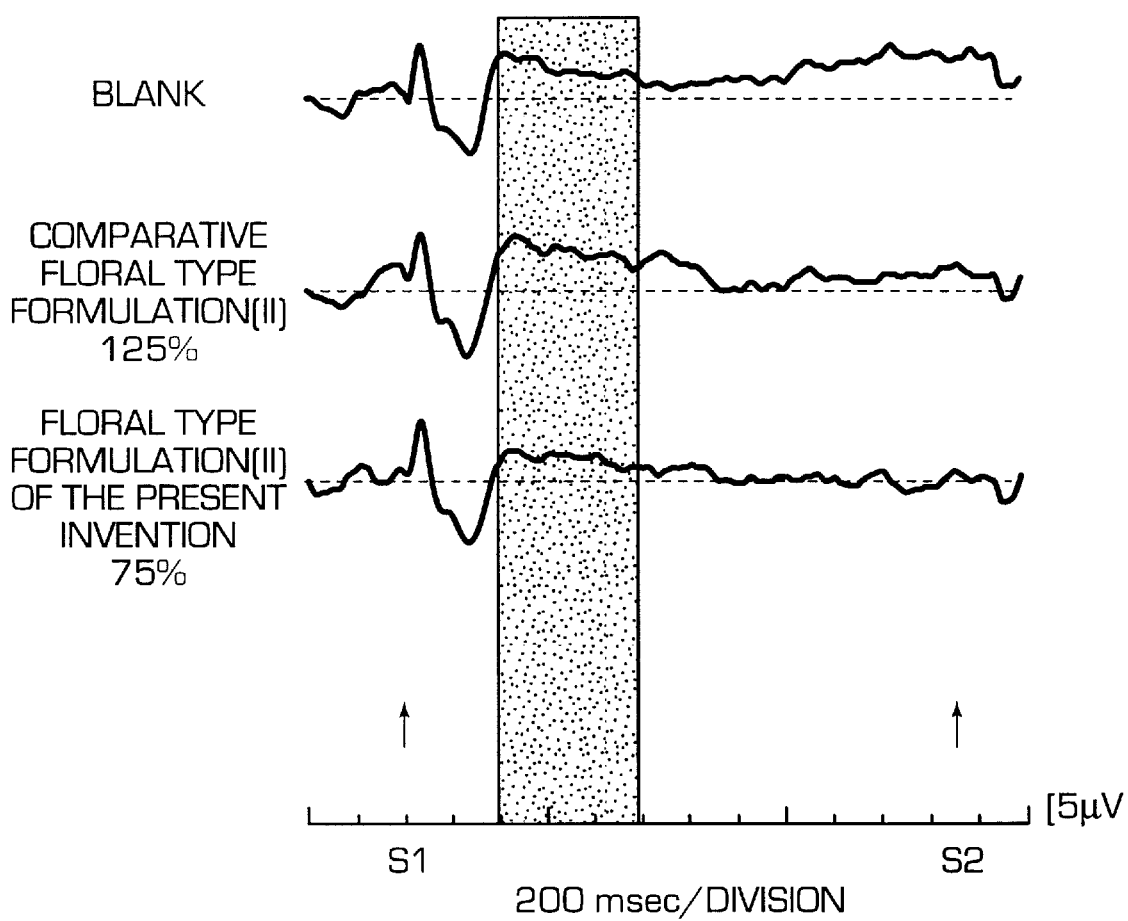

SEDATIVE EFFECT-PROVIDING FRAGRANCE MODIFIER

This is a Continuation of application Ser. No. 08/126,195 filed Sep. 24, 1993, now abandoned.

FIELD OF THE INVENTION

This invention relates to a fragrance modifier which provides a sedative effect.

Fragrance compounds can be provided with a sedative effect by blending them with 1,3-dimethoxy-5-methylbenzene which is known as a compound having a sedative effect. In consequence, the sedative effect of this compound can be reproduced in various articles such as perfumes, Colognes, shampoos, rinses, skin cares, body shampoos, body rinses, body powders, air fresheners, deodorants, baths and the like, by blending them with a fragrance composition which contains this compound.

BACKGROUND OF THE INVENTION

It is an unavoidable fact that stress, insomnia and the like symptoms are caused at our daily life as one of the "modern diseases" in our time. In consequence, releasing the tension and sound sleep have become of strong interest in these years, and much attention is being denoted to the effect of fragrance compounds to excite or sedate human consciousness as one of their functions.

Fragrance-inherent functions have been used in various forms in daily life since ancient times from generation to generation with great interest.

For example, flowers or essential oils of lavender and chamomile have been used as drinks and baths having a sedative effect, or as herbs with the aim of inducing sound sleep by arranging them in bedrooms. Recently, attempts have been made to confirm and elucidate such traditionally handed down functions through modern science, and several results have been obtained and put into practical use. For example, fragrance compositions containing sandalwood oil, lavender oil, chamomile oil and the like as sedative components and jasmine oil, ylang—ylang oil, basil oil and the like as stimulative components have already been proposed for instance in JP-A-63-199292 and JP-A-63-199293 (the term "JP-A" as used herein means an "unexamined published Japanese patent application").

These known components are natural essential oils used as general fragrance compounds which also contain compounds having no sedative effects. Also, since each of these components is used in the form of natural essential oil, its application is limited to the inherent fragrance compound of each natural essential oil, and, even if it has a sedative effect, it can cope with the taste and diversity preferences of the modern people only within a limited range because the moderns sometimes dislike other components contained in the oil. In addition, more objective evaluation of the fragrance functions by scientific means is required in these days rather than the conventional subjective evaluation, but it is difficult to develop a fragrance composition from which constant levels of physiological and psychological effects can be expected.

In consequence, it is necessary to confirm effects of formulation materials which can be used in various fragrance types, in order to develop a stable and preferable fragrance composition having a wide range of fragrance types.

SUMMARY OF THE INVENTION

In view of the above, it therefore becomes objects of the present invention to confirm sedative effect of a synthetic single aroma chemical, to develop a preferable fragrance composition having diversity of fragrance types making use of the synthetic single aroma chemical as a fragrance modifier and to provide the resulting fragrance product with sufficient sedative function.

Accordingly, the present invention relates to a fragrance composition which contains 1,3-dimethoxy-5-methylbenzene in an amount of from 0.01 to 30 parts by weight as a sedative effect-providing fragrance modifier and to its use.

Other objects and advantages of the present invention will be made apparent as the description progresses.

BRIEF DESCRIPTION OF THE DRAWINGS

FIG. 1 is a graph showing a relative value of an area on a chart obtained by CNV measurement during a period of from 400 to 1,000 msec after a sound stimulation, calculated based on a control (odorless stimulation) area which is taken as 100%, wherein a value larger than 100% indicates a stimulative tendency and a value smaller than 100% indicates a sedative tendency.

FIG. 2 is a graph showing a relative value in relation to a jasmine type formulation of Test Example 2, calculated in the same manner as used in FIG. 1.

FIG. 3 is a chart of CNV measurement in relation to a jasmine type formulation of Test Example 2.

FIG. 4 is a graph showing a relative value in relation to a floral type formulation (I) of Test Example 2, calculated in the same manner as used in FIG. 1.

FIG. 5 is a chart of CNV measurement in relation to a floral type formulation (I) of Test Example 2.

FIG. 6 is a graph showing a relative value in relation to a floral type formulation (II) of Test Example 2, calculated in the same manner as used in FIG. 1.

FIG. 7 is a chart of CNV measurement in relation to a floral type formulation (II) of Test Example 2.

In these drawings, AA, BB and CC indicate three subjects participated in the tests.

DETAILED DESCRIPTION OF THE INVENTION

Negative and slow changes in the electric potential, so-called "contingent negative variation" (to be referred to as "CNV" hereinafter), were measured for use in the screening of a sedative compound which is one of the objects of the present invention. CNV is a slow cerebral potential variation which is related to psychological processes such as attention, expectation, anticipation and the like and to changes in the level of consciousness.

In the experimental method for the screening of a compound of interest, a light signal which means start of movement is emitted 2.3 seconds after a stimulation with a warning sound, and one has to push a button simultaneously with the recognition of the light. During repetition of a series of such process, an aromatic sample is arranged about 10 cm under the person's nose so that its scent can be recognized constantly with breathing. An electrode for the measurement of CNV is set on the forehead to record electric potential between the forehead and an earlobe. It has already been reported that the CNV amplitude increases when caffeine having a stimulative effect is applied, while the amplitude decreases when nitrazepam having a sedative effect is applied.

Such variation occurs significantly during an initial interval of 400 to 1,000 msec after the sound stimulation, and the variation area is expressed by percentage based on a blank (odorless stimulation) which is taken as 100%. In this instance, the scent is presented in accordance with the Latin square.

The relative area larger than 100% indicates a stimulative effect, and smaller than 100% a sedative effect. Ogata et al. have examined a large number of natural essential oils making use of the contingent negative variation method and reported that compounds having sedative effects and stimulative effects are contained in the essential oils (Shigeki Ogata et al., Abstract of Papers, The Japanese 20th Symposium on Taste and Smell, p.149, 1986).

The compound 1,3-dimethoxy-5-methylbenzene to be used in the present invention is contained in a large quantity in modern roses such as Hybrid T especially at the time of flowering, and it has a gentle and fresh green note with a sedate aroma. It is known that this compound is not contained in roses belonging to *Rosa damascena* and *Rosa centifolia* which are used as fragrance materials, but in modern rose varieties as an aromatic component in an approximate amount of from several to 70% (Shoji Nakamura; *Perfumer & Flavorist;* 12, JUNE/JULY, 43–45, 1987). However, stimulative or sedative effect has not been confirmed yet in this compound.

As described in the foregoing, the present invention relates to a fragrance composition in which 1,3-dimethoxy-5-methylbenzene is blended as a sedative effect-providing fragrance modifier, and the fragrance composition can be used in perfumes, Colognes, shampoos, rinses, skin cares, body shampoos, body rinses, body powders, air fresheners, deodorants, baths and the like, if necessary in combination with auxiliary materials. The amount of 1,3-dimethoxy-5-methylbenzene to be blended in the fragrance composition may be determined optionally, taking purpose of its use and the like into consideration, but it may be used in an amount of generally from 0.01 to 30% by weight, preferably from 0.1 to 10% by weight. The fragrance modifier exerts its sedative effect when it is contained in an amount of 0.01% by weight or more, but its content exceeding 30% by weight does not exert proportionally increased sedative effect and is not preferable when its balance with other aromatic components is taken into consideration.

As described above, 1,3-dimethoxy-5-methylbenzene has a gentle and sedate aroma, and it does not exert significant influence upon quality and tone of the scent of other aromatic components when mixed therewith.

EXAMPLES

The following examples are provided to further illustrate the present invention. It is to be understood, however, that the examples are for purpose of illustration only and are not to be construed to limit the scope of the invention.

Test Example 1

A great difference in the scent between the roses belonging to *Rosa damascena* and *Rosa centifolia* which are cultivated as fragrance materials and the roses of the modern varieties is that the former roses do not contain 1,3-dimethoxy-5-methylbenzene. In the present invention, 1,3-dimethoxy-5-methylbenzene (to be referred to as "DMB" hereinafter in some cases) is used in two concentrations, 1% and 10% each in diethylphthalate solution, to measure its effect on CNV. That is, the aforementioned experiment was carried out with three healthy female adults as subjects in the test. As the results, all the subjects responded to both 1% and 10% concentrations with a relative value of 100% or less, it confirmed the compound had a sedative effect. Results of the measurement (relative value) are shown in FIG. 1.

Test Example 2

Next, DMB whose sedative effect as a single chemical was confirmed in the above test was added to a fragrance formulation whose stimulative effect has already been confirmed, in order to examine effect of the compound in the fragrance formulation. That is, a jasmine type formulation and floral type formulations (I) and (II) whose stimulative effects have already been confirmed were checked for their effects on CNV in the same manner as described in Test Example 1 with three healthy female adults as subjects in the test. As the results, all the subjects showed the same response indicating that the stimulative effect of these fragrance formulations was changed into sedative effect by the addition of DMB. Formulation of each of the used fragrance compositions is shown in the following, and the results of measurement are shown in FIGS. 2 to 7.

| Jasmine type formulation | | |
|---|---|---|
| | (parts by weight) | |
| | Control plot | Test plot |
| beeswax absolute | 1 | 1 |
| benzyl acetate | 20 | 20 |
| benzyl alcohol | 4 | 4 |
| cis-3-hexenyl benzoate | 1 | 1 |
| cis-jasmone | 2 | 2 |
| eugenol | 1 | 1 |
| geranyl linalool | 5 | 5 |
| indole | 1.5 | 1.5 |
| isophytol | 10 | 10 |
| linalool | 8 | 8 |
| benzyl benzoate | 10 | 10 |
| phytol | 35 | 35 |
| ethyl alcohol | 1.5 | 1.5 |
| DMB | — | 2 |
| | 100 | 102 |

| Floral type formulation (I) | | |
|---|---|---|
| | (parts by weight) | |
| | Control plot | Test plot |
| n-nonanal 10% | 0.1 | 0.1 |
| benzyl benzoate | 1 | 1 |
| citronellol | 10 | 10 |
| citronellyl acetate | 0.2 | 0.2 |
| citronellyl formate | 0.1 | 0.1 |
| eugenol | 0.5 | 0.5 |
| geraniol | 12.5 | 12.5 |
| geranyl acetate | 0.3 | 0.3 |
| cic-3-hexenol | 0.2 | 0.2 |
| nerol | 2.5 | 2.5 |
| phenylethyl alcohol | 71 | 71 |
| phenylethyl acetate | 1.5 | 1.5 |
| rose oxide | 0.1 | 0.1 |
| DMB | — | 2 |
| | 100 | 102 |

Floral type formulation (II)

| | (parts by weight) | |
|---|---|---|
| | Control plot | Test plot |
| aldehyde base | 4 | 4 |
| amyl salicylate | 2.5 | 2.5 |
| benzyl acetate | 1.5 | 1.5 |
| benzyl salicylate | 10 | 10 |
| bergamot oil | 6 | 6 |
| carnation base | 3 | 3 |
| coumarin | 0.2 | 0.2 |
| 1,3,4,6,7,8-hexahydro-4,6,6,7,8,8-hexamethyl cyclopenta-γ-2-benzopyran | 4 | 4 |
| green base | 6 | 6 |
| jasmine base | 10 | 10 |
| methyl ionone | 5.5 | 5.5 |
| muguet base | 10 | 10 |
| musk ketone | 4.5 | 4.5 |
| phenylethyl alcohol | 4 | 4 |
| rose base | 4 | 4 |
| Santalex T (Takasago International Corp.) | 2.5 | 2.5 |
| ylang-ylang oil | 2.5 | 2.5 |
| dipropylene glycol | 19.8 | 19.8 |
| DMB | — | 2 |
| | 100 | 102 |

Thus, as is evident from the results shown in the drawings attached hereto, a preferable fragrance composition having a sedative effect can be obtained by adding DMB in an appropriate amount to a fragrance composition having a stimulative effect, without spoiling original aromatic tone of the fragrance.

Inventive Example 1

Preparation of bath powder

| | parts by weight |
|---|---|
| sodium bicarbonate | 70 |
| anhydrous sodium sulfate | 28.8 |
| fragrance (floral type formulation (I) of Test Example 2) | 1 |
| color Y-202-1 | 0.2 |
| (total) | 100 |

After making the above components except for the fragrance into a uniform mixture using a V type mixer, the floral type formulation (I) of Test Example 2 containing 2% DMB was added to the mixture and mixed thoroughly to obtain uniformly mixed bath powder.

Inventive Example 2

Preparation of an air freshener (gel type)

| | parts by weight |
|---|---|
| carrageenan | 3 |
| propylene glycol | 2 |
| propylparaben | 0.3 |
| fragrance (jasmine type of Test Example 2) | 5 |
| water | 89.7 |
| (total) | 100 |

Carrageenan, propylene glycol (a fixative) and propylparaben (an antiseptic) were mixed with stirring while adding water, and the resulting mixture was heated to a temperature of about 80° C. with gentle stirring. While stirring the thus treated mixture using a homomixer (Tokushu Kika Kogyo Co., Ltd.) at 3,000 rpm and at a temperature of about 65° C., the jasmine type formulation of Test Example 2 containing 2% DMB was added the mixture to make a uniform phase. Thereafter, the resulting mixture was poured into an appropriate container and spontaneously cooled to obtain a gel type air freshener.

Inventive Example 3

Preparation of an air freshener (liquid type)

| | parts by weight |
|---|---|
| 95% ethanol | 25 |
| surface active agent | 5 |
| fragrance (floral type formulation (II) of Test Example 2) | 3 |
| water | 67 |
| (total) | 100 |

Above components except for water were mixed together, and, while gently stirring the mixture, water was added to obtain a uniformly mixed liquid type air freshener. In this instance, polyoxyethylene nonylphenyl ether EO–13 was used as the surface active agent.

Preparation of a deodorant (liquid type)

| | parts by weight |
|---|---|
| undiluted deodorant solution FS-500M (Shiraimatsu Shinyaku Co., Ltd.) | 5 |
| 95% ethanol | 10 |
| surface active agent | 10 |
| 1% DMB (in diethyl phthalate solution) | 10 |
| water | 65 |
| (total) | 100 |

Above components except for water were mixed together, and, while gently stirring the mixture, water was added to obtain a liquid type deodorant. In this instance, polyoxyethylene nonylphenyl ether EO-10 was used as the surface active agent.

Inventive Example 5

Preparation of a deodorant (aerosol type)

|  | parts by weight |
|---|---|
| undiluted deodorant solution FS-500M (Shiraimatsu Shinyaku Co., Ltd.) | 5 |
| 95% ethanol | 20 |
| 1% DMB (in diethyl phthalate solution) | 10 |
| water | 40 |
| liquefied petroleum gas | 25 |
| (4.0 kg/cm$^2$ 20° C.) | |
| (total) | 100 |

An aerosol type deodorant was obtained by uniformly mixing above components except for liquefied petroleum gas, putting a predetermined amount of the mixture into an aerosol container which is subsequently equipped with a valve, and then charging the resulting container with liquefied petroleum gas.

As has been described in the foregoing, 1,3-dimethoxy-5-methylbenzene used in the present invention can exhibit a sedative effect not only by itself but also when mixed with various formulations of jasmine, floral and the like types having stimulative effects. Also, since a single chemical is used as an active ingredient, the present invention is more effective than the sedative function of natural essential oil from a viewpoint of sedation. In addition, since 1,3-dimethoxy-5-methylbenzene itself has a mild scent, its sedative effect can be obtained without altering original fragrance of interest.

While the invention has been described in detail and with reference to specific embodiments thereof, it will be apparent to one skilled in the art that various changes and modifications can be made therein without departing from the spirit and scope thereof.

What is claimed is:

1. A sedative fragrance composition comprising (a) 1,3-dimethoxy-5-methylbenzene in an amount of from 0.01 to 30% by weight as a fragrance modifier, and (b) a stimulative component, wherein said stimulative component is a jasmine formulation.

2. A sedative fragrance composition as in claim 1, wherein the sedative fragrance composition has a relative value of less than 100% in a CNV measurement.

3. A process for imparting sedative effect to a fragrance product by blending the fragrance product with the sedative fragrance composition of claim 1.

4. A process for imparting sedative effect to a fragrance product by blending the fragrance product with a fragrance composition which contains (a) 1,3-dimethoxy-5-methylbenzene in an amount of from 0.01 to 30% by weight as a fragrance modifier, and (b) a stimulative component selected from the group consisting of a jasmine formulation and a floral formulation, said fragrance composition having a relative value of less than 100% in a CNV measurement.

5. A sedative fragrance composition comprising (a) 1,3-dimethoxy-5-methylbenzene in an amount of from 0.01 to 30% by weight as a fragrance modifier, and (b) a stimulative component, wherein said stimulative component is selected from the group consisting of jasmine oil, ylang—ylang oil and basil oil.

6. A sedative fragrance composition as in claim 5, wherein the sedative fragrance composition has a relative value of less than 100% in a CNV measurement.

7. A process for imparting sedative effect to a fragrance product by blending the fragrance product with the sedative fragrance composition of claim 5.

8. A process for imparting sedative effect to a fragrance product by blending the fragrance product with the sedative fragrance composition of claim 6.

* * * * *